United States Patent
Taniguchi et al.

(10) Patent No.: US 8,145,325 B2
(45) Date of Patent: Mar. 27, 2012

(54) MOUTH CLEANING DEVICE

(75) Inventors: Shinichi Taniguchi, Hikone (JP);
Suehisa Kishimoto, Hikone (JP);
Tomohiro Kunita, Hikone (JP); Hiroaki Shimizu, Hikone (JP); Atsushi Takahashi, Kyoto (JP); Masayoshi Nagayama, Takaishi (JP); Yumi Hanato, Kawachinagano (JP); Wataru Sanematsu, Hirakata (JP); Yukihiro Masuda, Neyagawa (JP)

(73) Assignee: Panasonic Electric Works Co., Ltd., Osaka (JP)

( * ) Notice: Subject to any disclaimer, the term of this patent is extended or adjusted under 35 U.S.C. 154(b) by 1194 days.

(21) Appl. No.: 11/905,641

(22) Filed: Oct. 3, 2007

(65) Prior Publication Data

US 2008/0086189 A1    Apr. 10, 2008

(30) Foreign Application Priority Data

Oct. 6, 2006 (JP) .................................. 2006-275681

(51) Int. Cl.
*A61N 1/05* (2006.01)
(52) U.S. Cl. ............ 607/134; 15/167.1; 604/20; 433/32
(58) Field of Classification Search .................. 15/167.7, 15/167.1; 433/62, 32, 216; 604/20; 607/134
See application file for complete search history.

(56) References Cited

U.S. PATENT DOCUMENTS

| | | | |
|---|---|---|---|
| 4,665,921 A * | 5/1987 | Teranishi et al. | 607/75 |
| 4,969,868 A * | 11/1990 | Wang | 604/20 |
| 5,133,102 A | 7/1992 | Sakuma | |
| 5,372,501 A | 12/1994 | Shalvi | |
| 7,566,839 B2 * | 7/2009 | Hukuba et al. | 200/61.45 R |
| 2006/0070195 A1* | 4/2006 | Morita et al. | 15/105 |
| 2007/0011836 A1* | 1/2007 | Brewer et al. | 15/220.1 |

FOREIGN PATENT DOCUMENTS

| | | |
|---|---|---|
| EP | 0 143 748 | 6/1985 |
| JP | 2004-041684 | 2/2004 |
| JP | 2005-192578 | 7/2005 |
| JP | 2006034569 A * | 2/2006 |
| JP | 2006/104463 | 10/2006 |

* cited by examiner

*Primary Examiner* — Carl H Layno
*Assistant Examiner* — Brian T Gedeon
(74) *Attorney, Agent, or Firm* — Bacon & Thomas, PLLC

(57) ABSTRACT

A mouth cleaning device includes a head portion provided with bristles and an electrode; and a grip portion provided with an electrode. Further, the mouth cleaning device includes a boosting circuit for boosting an output voltage of a battery serving as a power source and applying the boosted voltage to the electrodes of the head portion and the grip portion; and a current limit circuit for limiting a current flowing from one electrode to the other via a human body.

10 Claims, 4 Drawing Sheets

MOUTH CLEANING DEVICE

FIELD OF THE INVENTION

The present invention relates to a mouth cleaning device for improving a hygienic condition inside a mouth by flowing a minute current into the mouth.

BACKGROUND OF THE INVENTION

In a conventional mouth cleaning device, an electric toothbrush or an ion toothbrush is known. The conventional mouth cleaning device removes plaque from teeth by flowing a minute current in a mouth, thereby enhancing the cleaning effect of brushing, metabolism of oral tissues or blood flow. For example, Japanese Patent No. 2560162 describes therein a toothbrush including a head portion having bristles and a handle portion having a battery. An electrode connected with one pole of the battery is arranged on a part of a surface of the handle portion, whereas an electrode connected with the other pole of the battery is arranged on the head portion. When a user inserts the head portion into a mouth while holding the handle portion, a minute current flows through the body from the hand holding the handle portion to the contact portions between the head portion and teeth or gums inside the mouth.

Further, to avoid an influence of a resistance variation of the human body upon a current, Japanese Patent Laid-open Application No. 2005-192578 (Reference 2) discloses a mouth cleaning device having a configuration in which the two electrodes respectively connected to an anode and a cathode of the battery are both accommodated in the head portion.

Since, however, the battery available on the market to be used in this type of mouth cleaning device has a voltage ranging from about 1.5 to 3 V and an average resistance of the human body is 80 k$\Omega$, it has been difficult to flow enough current to sufficiently obtain a desired effect.

Moreover, though the average resistance value of the human body is 80 k$\Omega$, it actually fluctuates from about 40 k$\Omega$ to 120 k$\Omega$. Therefore, when a battery having a voltage of 3 V is used, a stationary current flowing in the device is made to vary from about 25 $\mu$A to 75 $\mu$A, so that an achieved effect varies greatly depending on individuals using the device.

Further, if it is attempted to increase a voltage by, e.g., connecting a plurality of batteries in series, the size of the device increases, which makes it costly and difficult to handle the device when brushing teeth. Further, with the increase of the voltage, there occurs a safety issue because a great amount of current may flow into the human body depending on the individuals.

At an initial stage of an electric conduction to the human body, a surge current can occur, which can inflict problems. Referring to FIG. 4, there is provided an equivalent circuit of a biological tissue, wherein a resistance value of a resistor R1 connected to a capacitor C in parallel is much larger than a resistance value of a resistor R2 connected to the capacitor C in series. In this case, at an initial stage of the electric conduction, a great amount of current (surge current) is flown in a path including the capacitor C for a short period of time until the capacitor C is charged, which is instantaneous. Then, upon the completion of the charging of the capacitor C, a minute current flows in a path including the resistor R1 having the larger resistance value. FIG. 5 is a graph showing the surge current and a stationary current thereafter.

The level of current which a living creature can perceive when the current flows in the mouth was investigated through animal experimentation. Animal behaviors indicating their perception of the current were observed at a current level of about 300 $\mu$A. Further, in an experiment for the human body in which a conduction path was set up from a mouth to a hand, a stationary current was about 40 $\mu$A and a surge current was about 1 mA. If the stationary current value is raised, the surge current also increases. Therefore, irritation is likely to be inflicted upon the human body. As a result, there occurs a safety issue.

As for Reference 2, if the inside of the mouth is filled with saliva, the two electrodes provided in the head portion having the bristles would be short-circuited via the saliva. In such case, a current hardly flows in the teeth or the gums, so that a desired effect cannot be obtained.

SUMMARY OF THE INVENTION

In view of the above, the present invention provides a mouth cleaning device capable of flowing an effective current to the human body without causing safety issues.

In accordance with an embodiment of the present invention, there is provided a mouth cleaning device including: a head portion provided with bristles and an electrode; a grip portion provided with an electrode; a boosting circuit for boosting an output voltage of a battery serving as a power source and applying the boosted voltage to the electrodes of the head portion and the grip portion; and a current limit circuit for limiting a current flowing from one electrode to the other via a human body. A voltage which is higher than a battery voltage and is capable of flowing a desired current can be obtained by providing a boosting circuit. Further, by providing a current limit circuit, surge current can be prevented and, overflowing of a current can also be prevented despite individual differences in resistance.

Preferably, a current limit value is less than or equal to about 300 $\mu$A. When the current is larger than the current limit value, i.e., about 300 $\mu$A, there occurs a concern that a human body can be stimulated.

Preferably, the current limit value is variable to overcome individual differences in resistance.

Preferably, the current has a pulse shape since the effect of massaging the gums is enhanced.

In accordance with the present invention, since a voltage which an appropriate current value is obtained by a boosting unit is applied, effects of removing teeth plaque inside a mouth, introducing fluorine on teeth, and massaging the gum can be properly obtained. Further, a current that causes the stimulation such as a surge current can not flow because the current is limited by the current limit circuit. Accordingly, safety is high.

BRIEF DESCRIPTION OF THE DRAWINGS

The objects and features of the present invention will become apparent from the following description of embodiments given in conjunction with the accompanying drawings, in which:

FIG. 3A shows a current waveform chart and FIG. 3B shows a voltage waveform;

DETAILED DESCRIPTION OF EMBODIMENTS

Figure 2:
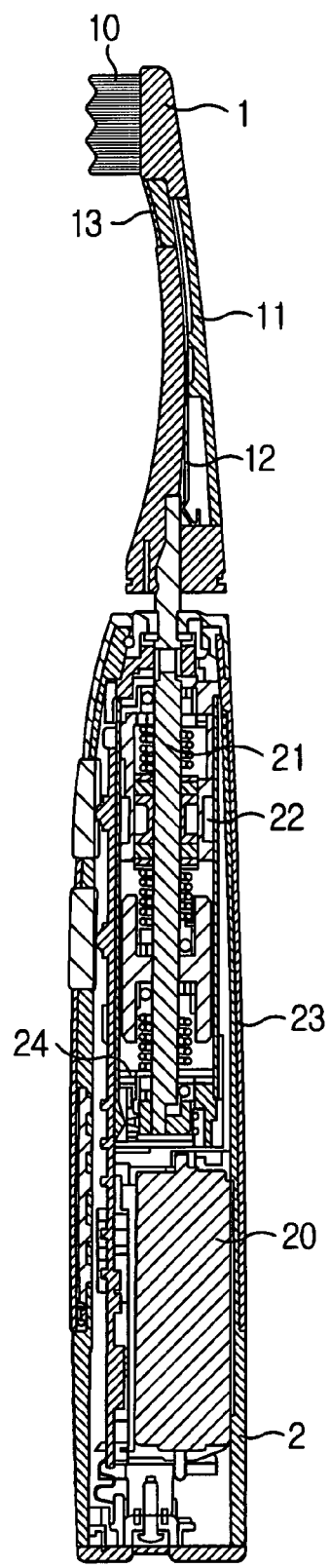
FIG. 2 sets forth a cross sectional view of an exemplary mouth cleaning device in accordance with the embodiment of the present invention.

The embodiments of the present invention will be described with reference to the accompanying drawings which form a part hereof. Referring to FIG. 2, a head portion 1 formed by arranging bristles 10 on one end side of a shaft 11 and a handle portion 2 accommodating therein a power source (e.g., battery or the like) 20. The handle portion 2 includes therein a driving shaft 21 having one end connected with the head portion 1, an actuator 22 for moving the driving shaft 21 in an axial reciprocating motion or the like, and a circuit board 24. Moreover, the handle portion 2 has an electrode 23 on an outer surface thereof, and the head portion 1 has an electrode 13 near roots of the bristles 10.

Figure 1:
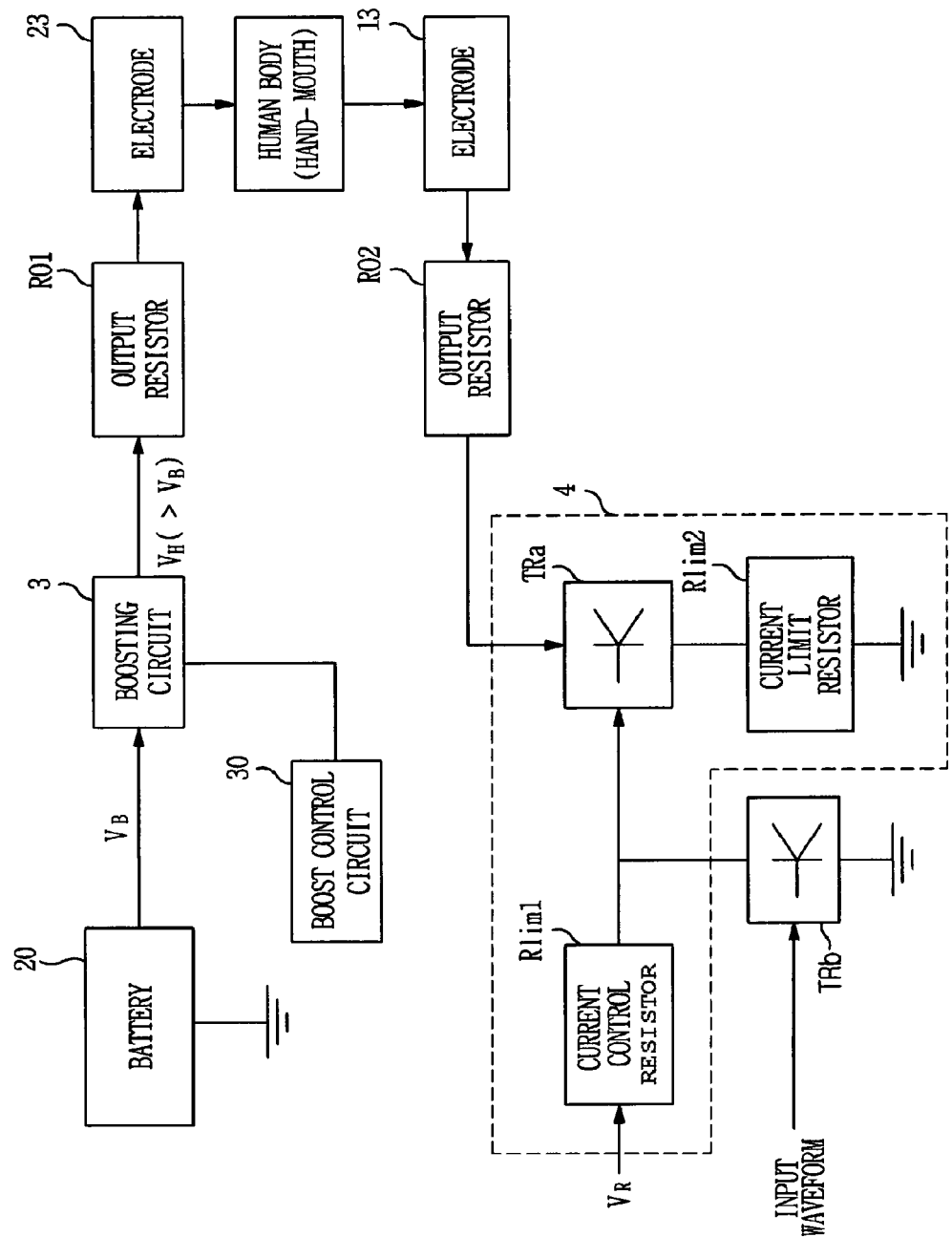
FIG. 1 is an exemplary block circuit diagram of an embodiment of the present invention.

As illustrated in FIG. 1, the electrode 23 is connected with the positive pole of the battery 20 via an output resistor Ro1 and a boosting circuit 3 mounted on the circuit board 24. Further, the electrode 13 of the head portion 1 is connected with the grounded negative pole of the battery 20 via a conduction plate 12 installed inside the shaft 11, the driving shaft 21, and the circuit board 24 (i.e., an output resistor Ro2, a current limit transistor TRa and limit resistor Rlim 2 mounted thereon).

The circuit board 24 has a current limit circuit 4 shown in FIG. 1, in addition to the boosting circuit 3. The current limit circuit 4, which is formed by the control resistor Rlim1, the current limit transistor TRa and a limit resistor Rlim2, generates a constant base current from a reference DC voltage $V_R$ (current limit control DC voltage) via the control resistor Rlim1, and limits a collector current that can flow through the current limit transistor TRa. The control resistor Rlim1 serves to adjust the reference DC voltage $V_R$, and can variably adjust a current limit when it is configured as a variable resistor, according to individual differences in a resistance of a human body, individual differences in reaction to a current and the like. It is preferable that the maximum value of the limited current which can flow through the human body is lower than or equal to about 300 µA.

The boosting circuit 3 boosts a battery voltage $V_B$ and generates a voltage $V_h$ ($V_h > V_E$) under the control of a boost control circuit 30. This voltage Vh is preferably a voltage which allows the supply of a current of a magnitude that enables required effects to be obtained even if a resistance of a conduction path including a human body is not uniform. For example, when a current of about 100 µA needs to flow on the assumption that a maximum resistance (including a contact resistance or the like) of the path including the human body is about 150 kΩ, the voltage Vh is about 15 V (=150 kΩ×100 µA).

Figure 3A:
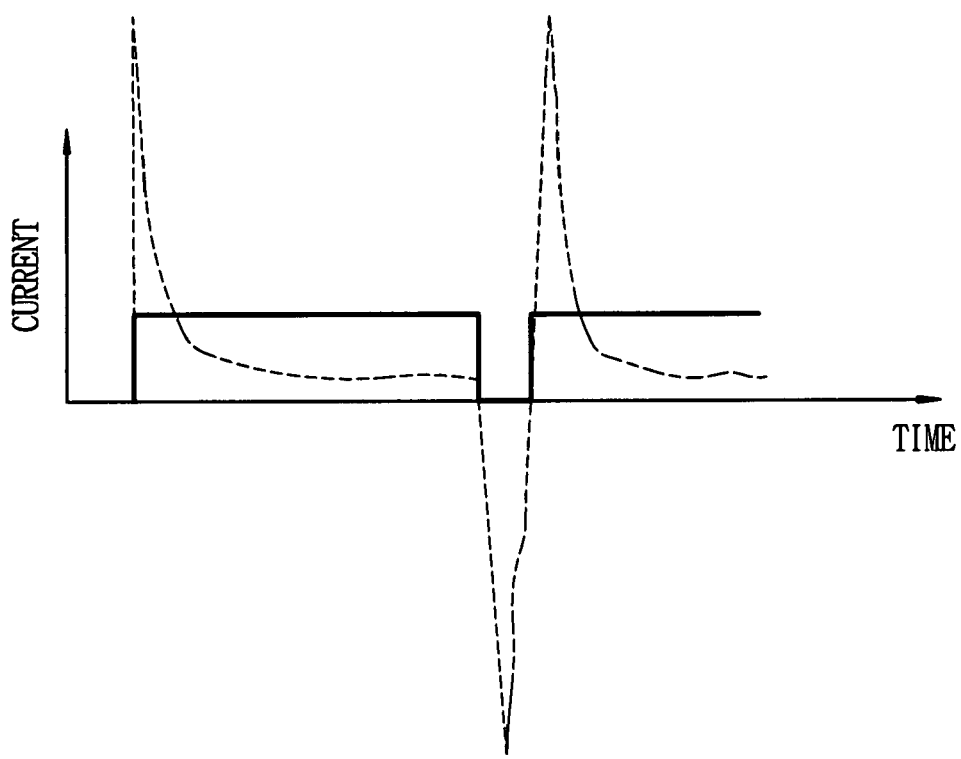
FIGS. 3A and 3B describe an exemplary operation of the mouth cleaning device in accordance with the embodiment of the present invention.
Figure 3B:
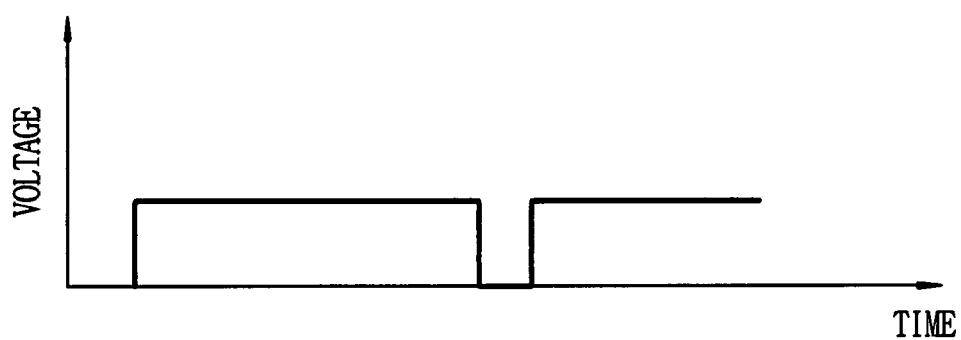
Figure 4:
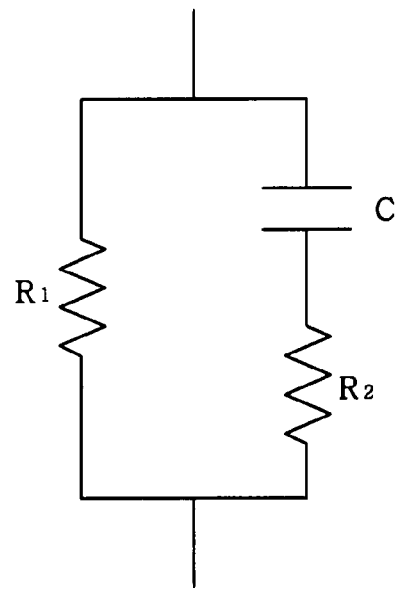
FIG. 4 presents an equivalent circuit of the human body.
Figure 5:
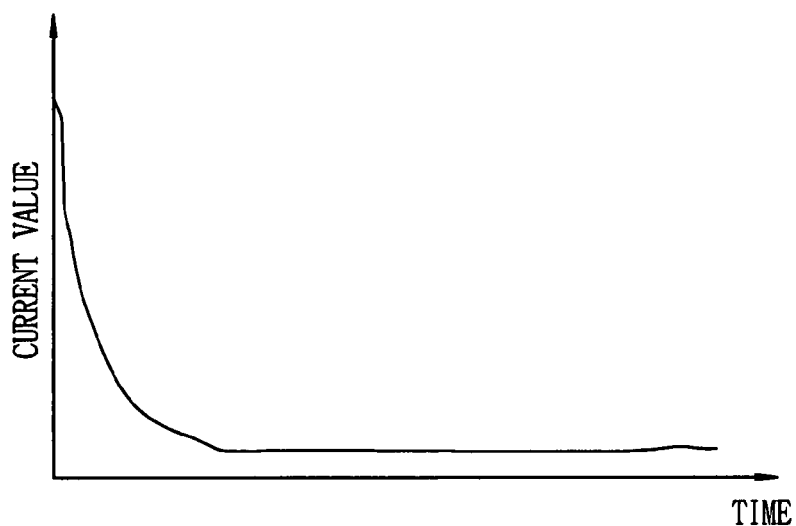
FIG. 5 depicts a current waveform showing a surge current.

If the handle portion 2 is held and the head portion 1 is inserted into the mouth in a state where the voltage Vh generated by the boosting circuit 3 is applied to the electrodes 13 and 23, the current flows from an output resistor Ro1 to the current limit transistor TRa via the electrode 23, the human body, the electrode 13, the conduction plate 12, the driving shaft 21 and an output resistor Ro2. However, the current is limited to, e.g., about 100 µA, by the aforementioned base current. Therefore, even when the resistance of the human body is low, the current, which is greater than or equal to about 100 µA, does not flow and, also, a surge current can be suppressed. Therefore, the current flowing in the human body is allowed to have a waveform drawn by a solid line in FIG. 3, thus inflicting no safety problem as caused in a conventional case indicated by a dashed line in FIG. 3.

The circuit configuration illustrated in FIG. 1 is just an example and can be varied in various ways. For example, the output resistors Ro1 and Ro2 can be omitted, and the configuration of the current limit circuit is not limited.

Moreover, as depicted in FIG. 1, there is provided a transistor TRb which temporarily blocks a current by reducing a base potential of the current limit transistor TRa to zero at regular intervals so that a pulsed current can flow through the human body. In particular, if the current flowing in the human body has a pulse shape of a frequency ranging from about 400 Hz to 15000 Hz, the effect of massaging the gums is enhanced.

The electrode 13 is a negative electrode to which a unipolar pulsed current is supplied to prevent elution of an electrode metal. When an electrode inserted into a mouth serves as an anode, teeth or gums serve as a cathode. In that case, a metal of the anode is eluted, and the eluted metal is deposited on the teeth or the gums serving as the anode.

In the above embodiment, though the mouth cleaning device is described to have the actuator 22 for moving the head portion 1, it is also possible to omit the actuator 22 (or any other substitute driving units for it).

While the invention has been shown and described with respect to the embodiments, it will be understood by those skilled in the art that various changes and modifications may be made without departing from the scope of the invention as defined in the following claims.

What is claimed is:

1. A mouth cleaning device comprising:
   a head portion provided with bristles and a first electrode;
   a grip portion provided with a second electrode;
   a boosting circuit for boosting an output voltage of a battery serving as a power source and applying the boosted voltage to the electrodes of the head portion and the grip portion;
   a current limit circuit for variably setting a limit value of a current flowing from one electrode to the other, the current limit circuit including a current limit transistor connected between the first electrode of the head portion and a negative pole of the battery; and
   a pulse circuit for changing the current flowing from one electrode to the other into a pulse shape by reducing a base potential of the current limit transistor to zero at regular intervals.

2. The mouth cleaning device of claim 1, wherein the limit value is less than or equal to about 300 µA.

3. The mouth cleaning device of claim 2, wherein the current has a pulse shape.

4. The mouth cleaning device of claim 1, wherein the current has a pulse shape.

5. The mouth cleaning device of claim 1, wherein the current limit circuit has a variable resistor for varying the limit value of the current flowing from one electrode to the other.

6. The mouth cleaning device of claim 1, wherein the current limit circuit has a variable resistor, the variable resistor generating a base current thereof to variably set the limit value of the current flowing from one electrode to the other.

7. A mouth cleaning device comprising:
   a head portion provided with bristles and a first electrode;
   a grip portion provided with a second electrode;
   a boosting circuit for boosting an output voltage of a battery serving as a power source and applying the boosted voltage to the electrodes of the head portion and the grip portion;

a current limit circuit for variably setting a limit value of a current flowing from one electrode to the other, the current limit circuit including a current limit transistor connected between the first electrode of the head portion and a negative pole of the battery; and a pulse circuit for changing the current flowing from one electrode to the other into a pulse shape by reducing a base potential of the current limit transistor to zero at regular intervals.

wherein the first electrode of the head portion is a negative electrode to which a unipolar pulsed current is supplied.

8. The mouth cleaning device of claim 7, wherein the current limit circuit has a variable resistor for varying the limit value of the current flowing from one electrode to the other.

9. The mouth cleaning device of claim 7, wherein the current limit circuit has a variable resistor, the variable resistor generating a base current thereof to variably set the limit value of the current flowing from one electrode to the other.

10. The mouth cleaning device of claim 7, wherein the limit value is less than or equal to about 300 µA.

* * * * *